United States Patent [19]

Kötzsch et al.

[11] 4,213,908

[45] Jul. 22, 1980

[54] SILICEOUS DIOXOLANE DERIVATIVES AND THEIR APPLICATION TO THE MANUFACTURE OF ORGANOSILANE ESTERS CONTAINING EPOXY GROUPS

[75] Inventors: Hans-Joachim Kötzsch, Rheinfelden; Hans-Joachim Vahlensieck, Wehr, both of Fed. Rep. of Germany

[73] Assignee: Dynamit Nobel Aktiengesellschaft, Troisdorf, Fed. Rep. of Germany

[21] Appl. No.: 635,533

[22] Filed: Nov. 26, 1975

Related U.S. Application Data

[62] Division of Ser. No. 469,937, May 14, 1974, Pat. No. 3,932,462, which is a division of Ser. No. 310,495, Nov. 29, 1972, Pat. No. 3,825,567.

Foreign Application Priority Data

Dec. 3, 1971 [DE] Fed. Rep. of Germany ....... 2159991

[51] Int. Cl.² ............................ C07F 7/08; C07F 7/18
[52] U.S. Cl. ................................................. 260/348.16
[58] Field of Search ......... 260/348 R, 348 SC, 348.16

[56] References Cited

FOREIGN PATENT DOCUMENTS

F15046  1/1956  Fed. Rep. of Germany .
1940205  2/1971  Fed. Rep. of Germany .

OTHER PUBLICATIONS

Searles et al., Jour. Am. Chem. Soc., vol. 82 (1960) pp. 2928–2931.

*Primary Examiner*—Norma S. Milestone
*Attorney, Agent, or Firm*—Sprung, Felfe, Horn, Lynch & Kramer

[57] ABSTRACT

Glycidyloxypropylalkoxysilanes are produced by thermal treatment of novel siliceous dioxolane derivatives of the formula:

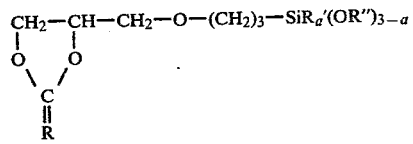

wherein a is 0 or 1 and R represents an oxygen radical or two hydrogen atoms and R' and R'' each represents an alkyl radical, wherein the R'' 's can be the same or different. The glycidyl products are useful as adhesives.

6 Claims, No Drawings

SILICEOUS DIOXOLANE DERIVATIVES AND THEIR APPLICATION TO THE MANUFACTURE OF ORGANOSILANE ESTERS CONTAINING EPOXY GROUPS

This is a division of application Ser. No. 469,937, filed May 14, 1974, now U.S. Pat. No. 3,932,462, which is a division of Ser. No. 310,495, filed Nov. 29, 1972, now U.S. Pat. No. 3,825,567, issued July 23, 1974.

BACKGROUND

Organosilanes which contain epoxy groups have for some years been attracting a great deal of technical interest. They are used, for example, as adhesives for the combination of certain organic polymers, such as epoxy resins or phenolic resins with glass fibers, fabrics or roving, and for improving adhesion in the bonding of sand molds. Successful attempts have already been made for the improvement of the adhesion between plastics and metals on the basis of the use of such silanes.

The synthesis of these epoxy organosilane esters has hitherto been possible through a variety of methods. For example, organosilane esters containing carbon double bonds are oxidized with peroxides to produce such epoxides. This method, however, is not generally applicable to the synthesis of the entire class of substances owing to poor compatibility with the sensitive silane esters. On the other hand, it suffers from by-products which necessarily arise from the peroxides and therefore it is economically unprofitable. Furthermore, the use on a large technical scale of the peroxides suitable for this procedure, such as peracetic acid, entails considerable safety risks.

Another known method of manufacturing epoxy organosilane esters is the catalytic addition of hydrogen silane esters onto the carbon double bond of a monoolefinic epoxy compound. The catalysts used for this purpose are essentially simple or complex compounds of nickel, platinum, rhodium or ruthenium.

The disadvantage of this process lies especially in the action of the basic epoxy group on the base-sensitive hydrogen silane esters. This leads on the one hand to competing disproportionation reactions with the formation of higher silane esters and hydrogen silanes. On the other hand, this basicity is so great that it has a poisoning effect on the catalysts. Since in this process a satisfactory transformation is not achieved until temperatures of 130° C. and up are reached, these competing reactions may become very undesirably evident. In addition, the catalysts also bring about the hydrogenation of the olefinic center of addition. Numerous attempts have therefore been made to overcome these disadvantages by complex variants at the central atoms of the catalysts, and gradual improvements have indeed been achieved, although it has not been possible to completely eliminate the described difficulties.

Inasmuch as the catalytic addition of chlorosilanes rather than the sensitive hydrogen silane esters runs into difficulties on account of the basicity of the epoxy compounds, attempts have also been made to use hydrogen fluorosilanes as starting materials. The epoxy organofluorosilanes thus obtained then have to be reesterified. This procedure again involves the disadvantage of the introduction of a two-stage process, while the known disadvantages of catalyst poisoning and of the competing hydrogenation reaction are not eliminated. In addition, working with hydrogen fluorosilanes requires the expensive safety measures and procedures which are necessarily involved in fluorine chemistry, so that higher first costs are involved in the application of this process.

THE INVENTION

It has now surprisingly been found that the above-described difficulties can be overcome simply by using as the starting products in the synthesis of silane esters containing epoxy groups siliceous dioxolane derivatives which have hitherto been unknown, and subjecting these new compounds to a thermal treatment in which the epoxy group containing silanes form with the yielding of highly volatile substances.

The subject of the invention is new siliceous dioxolane derivatives of the general formula:

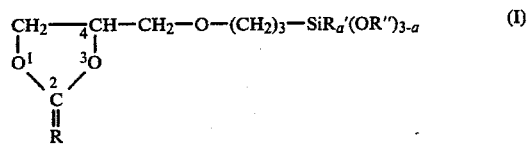

in which a=0 or 1 and R represents an oxygen radical or two hydrogen atoms and R' and R" represent identical or different alkyl radicals, as well as the use of these derivatives in a process for the manufacture of 3-glycidyloxypropylalkoxysilanes which process is characterized in that the siliceous dioxolane derivatives are subjected to a thermal treatment which results in the yielding of $CO_2$ or formaldehyde.

The 3-glycidyloxypropylalkoxysilanes are of the formula:

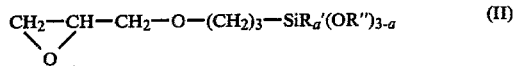

wherein a, R' and R" are as defined in reference to (I).

In the above general formulas, R' and R" represent a lower alkyl radical with preferably 1 to 4 carbon atoms e.g. methyl, ethyl, propyl, isopropyl, and n-, s-, t- and iso-butyl.

The process of the use of the siliceous dioxolane derivatives may be performed both at normal pressure or in vacuo; e.g. 760 to <1 mm of Hg. The yielding of $CO_2$ or formaldehyde takes place at temperatures between about 130° and 240° C., preferably between about 140° and 180° C.

The cleavage is accelerated, especially when catalysts such as CaO are additionally used.

The splitting off of $CO_2$ or formaldehyde may also be performed by operating in vacuo, it being desirable to operate at the boiling temperature under the corresponding vacuum. Since the glycidyl silane that forms has a lower boiling point than the starting compound, this procedure presents the advantage that the desired end product can be separated immediately from the reaction chamber by interposing a suitable reflux column. The temperature above about 300° C. should preferably be avoided. The temperature should not exceed the decomposition temperature of the substrates. The splitting off of $CO_2$ or formaldehyde can also be carried out in the presence of basic metal oxides. This method has the advantage that the temperature, for a given rate of splitting off, can be lower. Catalytic amounts show a significant effect; stoichiometric amounts can be used.

The alkaline earth oxides or other basic metal oxides, such as zinc oxide, or the alkaline earth carbonates, are given as examples. These compounds are used preferably in quantities catalytic or stoichiometric to the starting siliceous dioxolane.

The compounds used as the starting substances are previously unknown compounds which are prepared by a method, employing a known type reaction, through the addition of 4-allyloxymethyl-2-oxo-1,3-dioxolane or 4-allyloxymethyl-1,3-dioxolane onto trialkoxy hydrogen silane or monoalkyl dialkoxy hydrogen silane, using platinum compounds as catalysts. The addition takes place at temperatures as low as 70° C., and, on account of the masking of the epoxy group, it does not have the above-described disadvantages entailed in the addition of compounds containing double bonds onto hydrogen silanes.

The following are given as examples of suitable starting substances: 4-(3-trimethoxysilylpropoxymethyl)-2-oxo-1,3-dioxolane or 4-(3, trimethoxysilylpropoxymethyl)-1,3-dioxolane. Both products lead to 3-glycidyloxypropyltrimethoxysilane, the former with the yielding of carbon dioxide, the latter with the yielding of formaldehyde.

EXAMPLE 1

3-glycidyloxypropyltrimethoxysilane

In a vacuum still with a 12-tray column containing a Multifil packing with a void volume of 96%, 840 grams of 4-(3'-trimethoxysilylpropoxymethyl)-2-oxo-1,3-dioxolane are heated with a bottom mass of 170 g of dry calcium oxide at 5 Torr (mm Hg) to a vigorous ebullition at which the temperature is 175° C. Within 3 hours, with a reflux ratio of 8, 701 grams of distallate having a boiling point of 124° to 126° C. (5 Torr) is obtained, which consists of virtually pure 3-glycidyloxypropyltrimethoxysilane and has the following characteristics:

$n_D^{20}$ 1.4278; $D_4^{20}$ 1.070

In its index of refraction, density and infrared spectrum, the substance is identical with authentic material.

EXAMPLE 2

2-oxo-4-(3'-trimethoxysilylpropoxymethyl)-1,3-dioxolane

The following reaction is performed in a 4-liter multiple-neck flask provided with a leaf stirrer, 2 dropper funnels, an internal thermometer and a reflux condenser with nitrogren gas shielding.

0.5 ml of a 1/100 molar solution of platinum hydrochloric acid in acetone is stirred into 316 g of 2-oxo-4-allyloxymethyl-1,3-dioxolane and the mixture is heated to 70° C. at atmospheric pressure. The heater is removed and the reaction is performed by adding simultaneously, drop by drop, 1464 grams of trimethoxysilane and 1580 g of 2-oxo-4-allyloxymethyl-1,3-dioxolane over a period of 3 hours, sustaining a reaction temperature of 70° C. by means of external cooling at atmospheric pressure. The mixture is stirred for one more hour at 70° C. The colorless to pale yellow crude product consists of 2-oxo-4-(3'-trimethoxysilypropoxymethyl)-1,3-dioxolane. Vacuum distillation delivers a yield of 3344 g. Boiling point: 155° C. (2 Torr); $n_D^{25}$ 1.4389; $D_4^{20}$ 1.184; the substance dissolves to form a clear solution in water.

Elemental analysis for $C_{10}H_{20}O_7Si$ (MW=280):

|  | C (%) | H (%) | Si (%) |
|---|---|---|---|
| calculated: | 42.8 | 7.14 | 10.0 |
| Found: | 42.9 | 7.3 | 10.2 |

The infrared spectrum shows a strong carbonyl band at 1799 cm$^{-1}$ which is to be associated with the C=O group on the dioxolane ring.

The reaction can also be carried out in the presence of CaO.

EXAMPLE 3

4-(3'-trimethoxysilylpropoxymethyl)-1,3-dioxolane

The reaction is performed similarly to Example 2 by placing 288 g of 4-allyloxymethyl-1,3-dioxolane in the reactor together with 0.5 ml of the same catalyst and adding simultaneously, drop by drop, 1464 g of trimethoxysilane and 1440 g of 4-alloxymethyl-1,3-dioxolane at 70° C. and atmospheric pressure.

The colorless to pale yellow crude product consists of 4-(3'-trimethoxysilylpropoxymethyl)-1,3-dioxolane. Vacuum distillation delivers a yield of 3179 g. Boiling point: 128° C. (2 Torr); $n_D^{25}$ 1.4362; $D_4^{20}$ 1.062. The substance dissolves in water to form a clear solution.

Elemental analysis for $C_{10}H_{22}O_6Si$ (MW=266):

|  | C (%) | H (%) | Si (%) |
|---|---|---|---|
| calculated: | 45.1 | 8.27 | 10.5 |
| found: | 45.3 | 8.4 | 10.4 |

What is claimed is:
1. Process of producing 3-glycidyloxypropylalkoxysilanes of the formula:

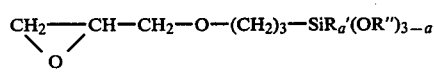

wherein a is 0 or 1 and R' and R" each represent an alkyl radical wherein the R"'s can be the same or different, which comprises heating a siliceous dioxolane of the formula:

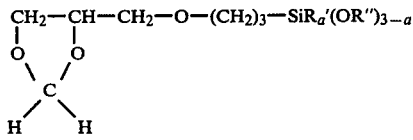

wherein a, R' and R" are as defined for the 3 glycidyl derivative, at a temperature of about 130°–240° C. and pressure and for a time sufficient to split off formaldehyde from said siliceous dioxolane to form said glycidyl derivative.

2. Process according to claim 1, the temperature being about 140°–180° C.

3. Process according to claim 1, the pressure being subatmospheric.

4. Process according to claim 1, the heating being performed in the presence a basic metal oxide inert with respect to said siliceous dioxolane and 3-glycidyl derivative.

5. Process according to claim 4, wherein said basic metal oxide is CaO.

6. Process according to claim 1, wherein said siliceous dioxolane is 4-(3'-trimethoxysilylpropoxymethyl)-1,3-dioxolane.

* * * * *